United States Patent
Zhang et al.

(10) Patent No.: US 12,043,434 B2
(45) Date of Patent: Jul. 23, 2024

(54) MEDICAL FLUID CONTAINER PREPARATION SYSTEM AND ASSEMBLY

(71) Applicants: BAXTER INTERNATIONAL INC., Deerfield, IL (US); BAXTER HEALTHCARE SA, Glattpark (CH)

(72) Inventors: Songqiang Zhang, Guangzhou (CN); Zhixiong Guo, Guangzhou (CN)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 517 days.

(21) Appl. No.: 17/427,560

(22) PCT Filed: Jan. 29, 2020

(86) PCT No.: PCT/US2020/015679
§ 371 (c)(1),
(2) Date: Jul. 30, 2021

(87) PCT Pub. No.: WO2020/160149
PCT Pub. Date: Aug. 6, 2020

(65) Prior Publication Data
US 2022/0133592 A1    May 5, 2022

(30) Foreign Application Priority Data
Jan. 30, 2019   (CN) .......................... 201910092658.2

(51) Int. Cl.
*B65B 55/10* (2006.01)
*A61J 1/10* (2006.01)
(Continued)

(52) U.S. Cl.
CPC ................. *B65B 55/10* (2013.01); *A61J 1/10* (2013.01); *A61J 1/1468* (2015.05); *A61M 1/287* (2013.01);
(Continued)

(58) Field of Classification Search
CPC ......... B65B 3/003; B65B 3/022; B65B 31/04; B65B 51/10; B65B 55/10; B65B 57/02;
(Continued)

(56) References Cited

U.S. PATENT DOCUMENTS

| 4,548,605 A | 10/1985 | Iwamoto et al. |
| 2003/0114788 A1 | 6/2003 | Keilman et al. |

(Continued)

FOREIGN PATENT DOCUMENTS

| CN | 201907685 U | 7/2011 |
| CN | 205076062 U | 3/2016 |

(Continued)

OTHER PUBLICATIONS

Chinese Office Action for Application No. 201910092658.2 dated Sep. 30, 2022.
(Continued)

*Primary Examiner* — John Kim
(74) *Attorney, Agent, or Firm* — K&L Gates LLP (57) ABSTRACT

A medical fluid container preparation system includes: a conveyor for conveying the medical fluid container, a water injector located along the conveyor, a mechanism for carrying the water injector towards and away from the medical fluid container; a sensor positioned and arranged to determine a location of the medical fluid container moving along the conveyor, and a control unit configured to read an output from the sensor and to cause (i) the mechanism to move the water injector towards the medical fluid container an amount based upon the location of the medical fluid container obtained from the sensor output and (ii) the water injector to inject a volume of water between the medical fluid container and an overpouch into which the medical fluid container is placed.

14 Claims, 5 Drawing Sheets

(51) Int. Cl.
    *A61J 1/14*     (2023.01)
    *A61M 1/28*     (2006.01)
    *B65B 3/00*     (2006.01)
    *B65B 31/04*     (2006.01)
    *B65B 51/10*     (2006.01)
    *B65B 57/14*     (2006.01)
    *B65B 57/16*     (2006.01)
    *A61J 1/20*     (2006.01)

(52) U.S. Cl.
    CPC .............. *B65B 3/003* (2013.01); *B65B 31/04* (2013.01); *B65B 51/10* (2013.01); *B65B 57/14* (2013.01); *B65B 57/16* (2013.01); *A61J 1/2089* (2013.01); *A61M 2209/045* (2013.01)

(58) Field of Classification Search
    CPC .. B65B 57/14; B65B 57/16; A61J 1/10; A61J 1/1468; A61J 1/16; A61J 1/2089; A61M 1/1668; A61M 1/28; A61M 1/287; A61M 2209/045
    See application file for complete search history.

(56) References Cited

U.S. PATENT DOCUMENTS

| | | |
|---|---|---|
| 2004/0146669 A1 | 7/2004 | Gollier et al. |
| 2008/0065043 A1 | 3/2008 | Bemer |
| 2015/0196700 A1 | 7/2015 | Childers et al. |
| 2016/0058663 A1 | 3/2016 | Kumar et al. |

FOREIGN PATENT DOCUMENTS

| | | |
|---|---|---|
| CN | 206031930 U | 3/2017 |
| CN | 106742247 A | 5/2017 |
| CN | 209776954 U | 12/2019 |
| JP | 2012130439 A | 11/2014 |

OTHER PUBLICATIONS

Chinese Search report for Application No. 2019100926582 dated Sep. 24, 2022.
European Office Action for Application No. 20708004.5 dated Mar. 13, 2023 (32 pages).

FIG. 6

MEDICAL FLUID CONTAINER PREPARATION SYSTEM AND ASSEMBLY

PRIORITY CLAIM

The present application is a national stage entry of International Application No. PCT/US2020/015679, filed Jan. 29, 2020, which claims priority to CN Application No. 201910092658.2, filed Jan. 30, 2019. The entire contents of each are incorporated herein by reference and relied upon.

TECHNICAL FIELD

This application relates to medical fluid containers, specially a medical fluid container preparation system and method.

BACKGROUND

Due to disease or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life-saving. One who has failed kidneys would not survive without replacing at least the filtration functions of the kidneys.

Peritoneal dialysis is one type of dialysis therapy commonly used to treat loss of kidney function. Peritoneal dialysis uses dialysis solution that is infused into a patient's peritoneal cavity through a catheter implanted in the cavity. The dialysis fluid contacts the patient's peritoneal membrane located in the peritoneal cavity. Waste, toxins and excess water pass from the patient's bloodstream through the peritoneal membrane and into the dialysis fluid. The transfer of waste, toxins, and water from the bloodstream into the dialysis fluid occurs due to diffusion and osmosis, i.e., an osmotic gradient occurs across the peritoneal membrane. Used dialysis fluid is drained from the patient's peritoneal cavity to remove waste, toxins and excess water from the patient. The above cycle is then repeated.

There are various types of peritoneal dialysis ("PD") therapies, including continuous ambulatory peritoneal dialysis ("CAPD"), automated peritoneal dialysis ("APD") and continuous flow peritoneal dialysis ("CFPD"). CAPD is a manual dialysis treatment, in which the patient connects an implanted catheter to a drain and allows used dialysis fluid to drain from the peritoneal cavity. The patient then manually allows fresh dialysis fluid to flow from a solution bag, through the patient's indewelling catheter and into the patient's peritoneal cavity. The patient may then disconnect the catheter from the solution bag to allows the dialysis fluid to dwell within the peritoneal cavity to transfer waste, toxins and excess water from the patient's bloodstream to the dialysate solution. After a dwell period, the patient may repeat the above manual procedure. In CAPD the patient performs several drain, fill, and dwell cycles during the day, for example, about four times per day.

Automated peritoneal dialysis ("APD") is similar to CAPD in that the dialysis treatment includes a drain, fill, and dwell cycle. APD machines, however, automatically perform three to four cycles of peritoneal dialysis treatment, typically overnight while the patient sleeps. The APD machines typically fluidly connect to an implanted catheter, to one or more solution bags and to a drain bag.

The APD machines pump fresh dialysate from the dialysate source, through the catheter, into the patient's peritoneal cavity and allow the dialysate to dwell within the cavity so that the transfer of waste, toxins and excess water from the patient's bloodstream to the dialysate solution can take place. The APD machines then pump spent dialysate from the peritoneal cavity, though the catheter, to the drain. APD machines are typically computer controlled so that the dialysis treatment occurs automatically when the patient is connected to the dialysis machine, for example, when the patient sleeps. That is, the APD systems automatically and sequentially pump fluid into the peritoneal cavity, allow for a dwell, pump fluid out of the peritoneal cavity and repeat the procedure.

As with the manual process, several drain, fill, and dwell cycles occur during APD. A "last fill" is typically used at the end of APD, which remains in the peritoneal cavity of the patient when the patient disconnects from the dialysis machine for the day. APD frees the patient from having to manually perform the drain, dwell, and fill steps.

As discussed above, both CAPD and APD involve the use of solution bags and drain bags. Preparing such bags requires a great deal of care and skill. The bags must not leak and must be made within certain specifications. The solution bags must also be sterilized to a level such that the solution is safe to be delivered to the patient. The bags must also be labeled properly, so that the user or caregiver may be certain that the patient is receiving the correct PD solution.

PD solution bags have historically been made of polyvinyl chloride ("PVC"). In certain jurisdictions, however, PVC has been prohibited for use in making solution bags or tubing that carries fluid to or from the patient. In response, non-PVC films and tubing have been developed. Putting those films and tubing into practice, however, has proven to be difficult. PVC is in general an easier material to work with than non-PVC materials. Non-PVC materials present many processing changes, which must be implemented, optimized and verified for regulatory purposes.

In one example, sterilization of solutions within non-PVC containers is more difficult than for similar PVC containers. A need exists accordingly for an improved non-PVC solution bag making and sterilization system and method.

SUMMARY

The present disclosure provides an improved medical fluid container and method of making the same. In one embodiment, the medical fluid container includes a medical fluid solution bag, e.g., a peritoneal dialysis solution bag, and a medical fluid drain bag, which are connected via tubing. The drain bag is in one embodiment made from polyvinyl chloride ("PVC"), while the solution bag is made from a material other than PVC ("non-PVC"). An overpouch is provided to hold the medical fluid or peritoneal dialysis ("PD") fluid set together, including the non-PVC solution bag, the PVC drain bag and tubing connecting the two bags.

One of the last steps in preparing the PD fluid set is to steam sterilize the bags while packaged together, so that the solution is safe to deliver to the patient, e.g., to the patient's peritoneal cavity. The heat of the steam destroys any microorganisms residing within the solution, which may harm the patient. The PVC material is generally better able to withstand steam sterilization temperatures than the non-PVC material. If a longer length of sterilization time suitable for PVC is also used for non-PVC, the non-PVC material may being to wrinkle. A shorter sterilization time is used accordingly for the non-PVC set, including the non-PVC solution bag and the PVC drain bag.

To aid the sterilization of the PD fluid set using the shorter sterilization time that is safe for non-PVC materials, the present disclosure attempts to create a more humid environment between the overpouch and the outside of the PD fluid set. The humid environment provides additional steam sterilization within the overpouch, which helps especially to sterilize difficult portions of the tubing between the bags, such as a Y-site where tubes from the solution bag and the drain bag come together. To create the humid environment, the present system and method perform at least one of: (i) add water between the overpouch and the PD fluid set and (ii) remove air from the overpouch.

To add water to the overpouch, a water pump is mounted in one embodiment adjacent to a conveyor that carries the PD fluid sets located within the overpouches. The overpouches are opened on one end and are located on the conveyor such that the open end faces the water pump. The location of the overpouch and PD fluid set may vary however in its distance from a side or edge of the conveyor having the water pump. That is, instead of requiring precise location of the overpouch and PD fluid set relative to the water pump, at least one sensor is provided that detects a location of the overpouch and PD fluid set, which is sent to a control unit that adjusts the water pump accordingly.

In an embodiment, multiple sensors are provided. The first sensor just discussed detects the location of the overpouch. The first sensor in various embodiments is located along the same side of the conveyor having the water pump, either upstream or downstream of the water pump. A second sensor is a trigger sensor, which senses a leading edge of the overpouch as it travels along the conveyor. The second sensor may be mounted above the conveyor and is used to trigger the pump sequence to inject a desired amount of water between the overpouch and the PD fluid set. A third sensor is a water detection sensor. The third sensor may be mounted directly adjacent to an output of the water pump and be used to ensure that water is delivered into the overpouch. In one embodiment, a source of water for injection ("WFI") is connected fluidly to the water pump. The third sensor causes the control unit to generate an alarm if np WFI is injected into the overpouch, for example, if the WFI source runs out of WFI.

The water pump in one embodiment outputs water through an outlet tube. A distal end of the outlet tube may be mounted to a motorized gantry mechanism that is positioned and arranged to move the pump outlet tube into the open end of the overpouch for a brief amount of time to inject the water. The output of the overpouch location sensor enables the control unit to know how far to move the end of the pump outlet tube to reach a desired location within the overpouch. The trigger sensor outputs to the control unit when it senses the leading edge of the overpouch. Concurrently, the overpouch location sensor detects how far the overpouch is from the pump side of the conveyor. The control unit receives the signals from both sensors, determines how far to move the pump outlet tube, and commands the motor of the gantry mechanism to perform the determined movement. The control unit also commands the pump to pump the desired amount of water into the overpouch when the pump outlet tube reaches its end of travel. The third sensor confirms to the control unit that the overpouch and PD fluid set have received the desired amount of water.

The overpouch and PD fluid set having the desired amount of water are then conveyed along the conveyer through a block containing a groove that forces the open end of the overpouch to partially close. The partial closure drives a desired amount of air out of the overpouch. The open end of the overpouch is welded closed immediately after the grooved block so that the overpouch cannot open back up to let air back in. The combination of the added water and the removed air creates a desired amount of humidity between the overpouch and PD fluid set for steam sterilization.

In light of the disclosure herein and without limiting the disclosure in any way, any aspect set forth in any one of Claims 1 to 20 may be combined with any other aspect of any other one or more of Claims 1 to 20, unless specified otherwise herein.

In other aspects of the present disclosure, any of the structure and functionality disclosed in connection with FIGS. 1 to 6 may be combined with any of the other structure and functionality disclosed in connection with FIGS. 1 to 6.

In light of the present disclosure and the above aspects, it is therefore an advantage of the present disclosure to provide a medical fluid container preparation system and method that improves sterility.

It is another advantage of the present disclosure to provide a medical fluid container preparation system and method that increases humidity within a container to be steam sterilized.

The advantages discussed herein may be found in one, or some, and perhaps not all of the embodiments disclosed herein. Additional features and advantages are described herein, and will be apparent from, the following Detailed Description and the drawings.

DETAILED DESCRIPTION

Figure 1:
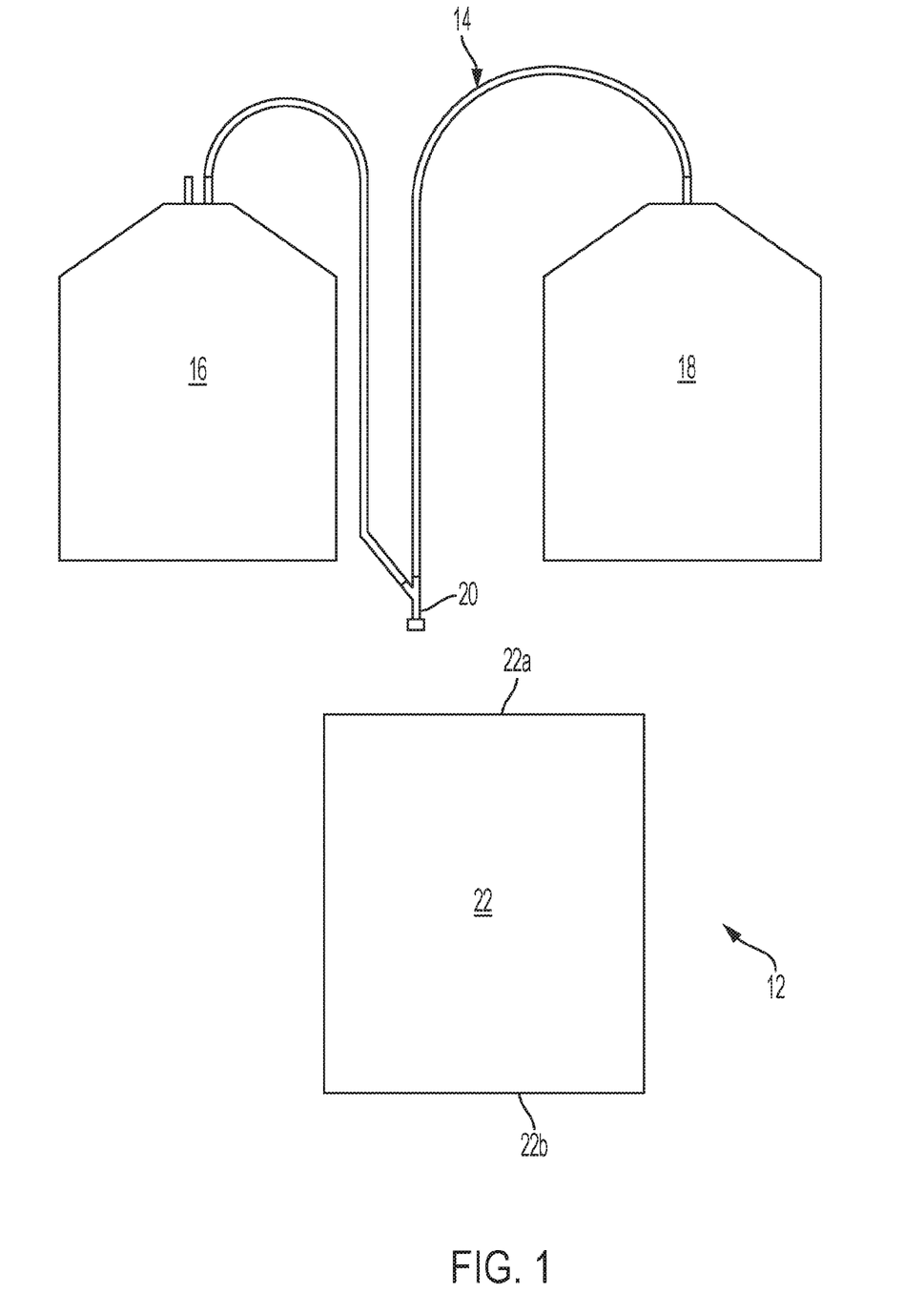
FIG. 1 is a top plan view of one embodiment of a medical fluid set and overpouch produced via the medical fluid container preparation system and associated methodology of the present disclosure.

Referring now to the drawings and in particular to FIG. 1, the components for forming an overpouched peritoneal dialysis ("PD") fluid set 12 using system 10 and its associated methodology are illustrated. The present system and method provides an improved medical fluid container and method of making the same. In the illustrated embodiment of FIG. 1, the medical fluid container includes a medical fluid solution bag 16, e.g., a PD solution bag, and a medical fluid drain bag 18, which are connected via tubing that meets at a Y-site 20. A PD patient connects Y-site 20 to the patient's indwelling catheter to allow manual dialysis to take place. If the patient is initially full of used PD fluid, the patient clamps the line leading to PD solution bag 16 and opens the line leading to drain bag 18, allowing effluent from the patient to drain to drain bag 18. The patient the reverses the clamps, allowing fresh PD solution to flow from PD solution bag 16 to the patient and dwell. The above process may then be repeated.

Drain bag 18 is in one embodiment made from polyvinyl chloride ("PVC"), while solution bag 16 is made from a material other than PVC ("non-PVC"). Solution bag 16, drain bag 18, the associated tubing and Y-site 20 together form a PD fluid set 14. An overpouch 22 is provided to hold PD fluid set 14 together in a sterilized manner, forming overpouched PD fluid set 12. In the illustrated embodiment, overpouch 22 includes an open end 22a to receive PD fluid set 14 and a closed end 22b against which PD fluid set 14 is pushed.

Figure 2:
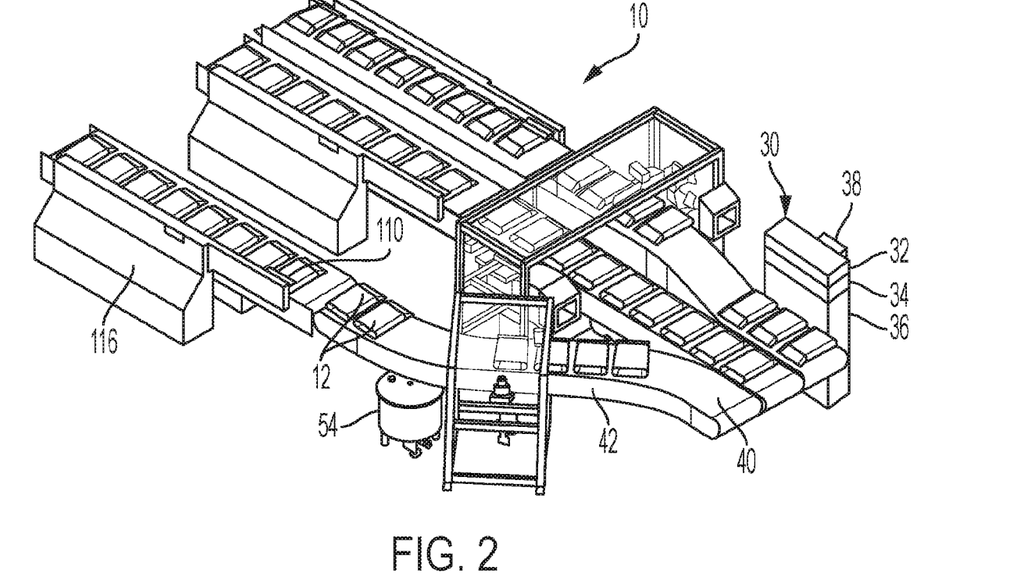
FIG. 2 is a perspective view of one embodiment of the medical fluid container preparation system and associated methodology of the present disclosure, illustrating multiple conveying lines.

One of the last steps in preparing the PD fluid set 14 is to steam sterilize the bags 16 and 18 while packaged together in overpouched PD fluid set 12, so that the solution is safe to deliver to the patient. In transitioning from PVC to non-PVC solutions bags 16, it has been found that the PVC material is generally better able to withstand steam sterilization temperatures than the non-PVC material. If a longer length of sterilization time suitable for PVC is also used for non-PVC, the non-PVC material may being to wrinkle. A shorter sterilization time is used accordingly for the non-PVC set, including the non-PVC solution bag and the PVC drain bag, FIG. 2 illustrates system 10, which aids the sterilization of the PD fluid set 14 using a shorter sterilization time, which is safe for non-PVC materials, by creating a more humid environment between overpouch 22 and the outside of PD fluid set 14. The humid environment provides additional steam sterilization within overpouch 22, which helps especially to sterilize difficult portions of the tubing between bags 16 and 18, such as a Y-site 20. To create the humid environment, system 10 and its associated methodology perform at least one of: (i) add water between overpouch 22 and PD fluid set 14 and (ii) remove air from within overpouch 22.

System 10 in FIG. 2 includes three conveyor lines, which are each controlled by a control unit 30, having one or more processor 32 to run one or more system 10 program stored on one or more memory 34, electronics 36 to communicate electrically with the three conveyor lines, and a user interface/display device 38 to allow an operator to setup, begin and review operation of system 10. While three conveyors are illustrated, conveyor 40 is highlighted. The other two conveyors in one embodiment have the same system 10 equipment and associated functionality as described for conveyor 40.

FIG. 2 further illustrates that overpouched PD fluid sets 12 travel along conveyor 40 generally from right to left and adjacent to a side or edge 42 of conveyor 40. A source of water for injection ("WFI") 54 is provided to supply WFI into overpouched PD fluid sets 12 as discussed in detail below. A block 110 is provided downstream from the water injection to squeeze air out of overpouch 22 before the open end 22a of the overpouch is welded closed via overpouch welder 116. The addition of water and the removal of air both help to increase the humidity of air trapped inside sealed overpouch 22 and corresponding overpouched PD fluid set 12.

Figure 3:
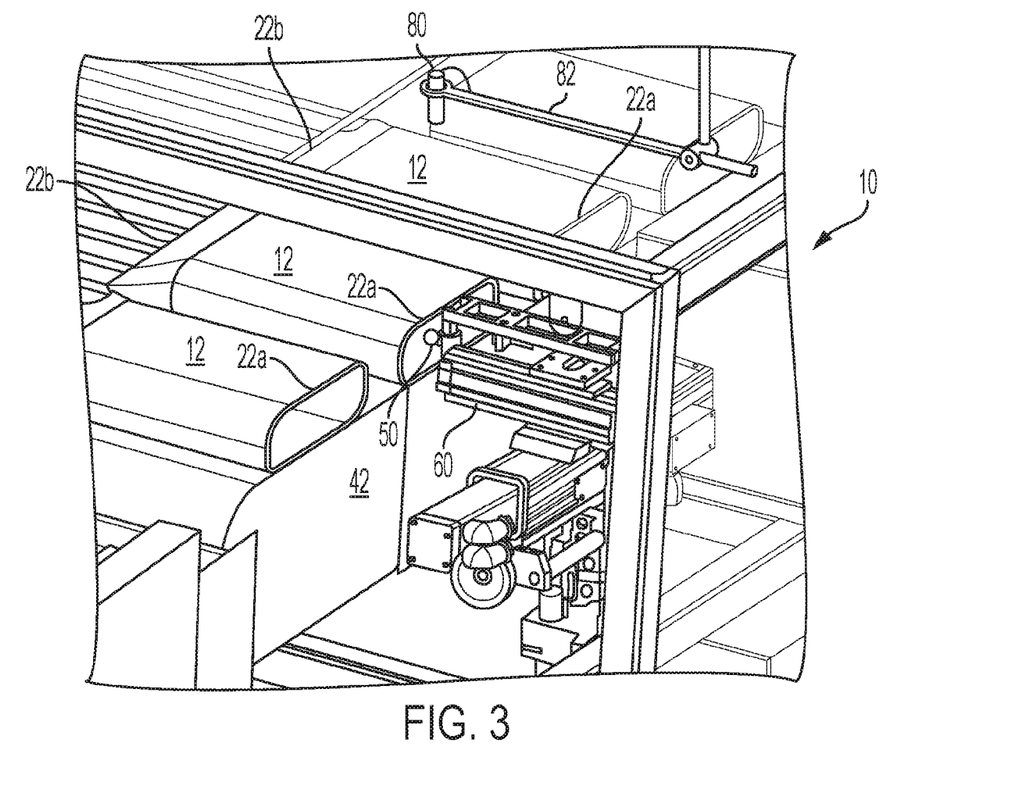
FIG. 3 is a perspective view of the medical fluid container preparation system of FIG. 2 showing a water injection portion in more detail.

FIG. 3 illustrates the water injection portion of system 10 in more detail. As illustrated, overpouched PD fluid sets 12 are oriented on conveyor 40 such that open ends 22a of overpouches 22 and overpouched PD fluid sets 12 face side or edge 42 of the conveyor. A water injector or pump 50 is provided to inject WFI within overpouched PD fluid sets 12. Suitable water injectors or pumps 50 are provided, for example, by HYBAR Systems Limited, Richmond Hill, Ontario, Canada and Ningbo, China. In an embodiment, water injector or pump 50 pumps from about 0.2 millimeters ("ml") to about 10 ml of WFI into overpouched PD fluid sets 12.

FIG. 3 further illustrates that water injector or pump 50 is mounted to and rides along with a motorized gantry or linear actuator 60. Motorized gantry or linear actuator 60 moves water injector or pump 50 towards side or edge 42 of conveyor 40 when an overpouched PD fluid set 12 is present, so that the WFI may be accurately and completely injected into the set. In an embodiment, both water injector or pump 50 and motorized gantry or linear actuator 60 are under the control of control unit 30.

Figure 4:
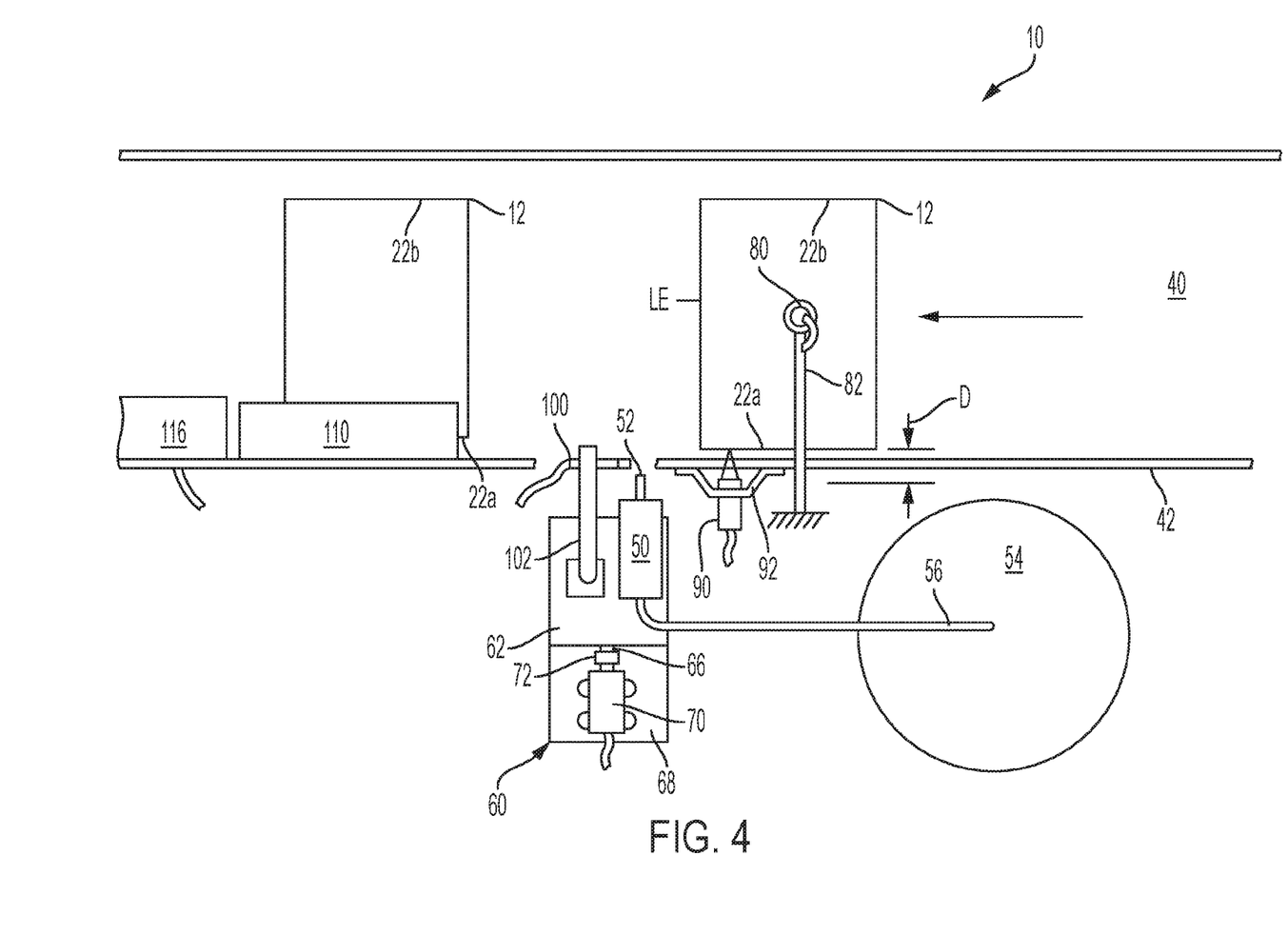
FIG. 4 is a top plan view of one embodiment of the medical fluid container preparation system and associated methodology of the present disclosure.

FIG. 4 illustrates system 10 from above, where overpouched PD fluid sets 12 having open ends 22a and closed ends 22b travel along conveyor from right to left. Water injector or pump 50 is illustrated having a tube 52 connected to its outlet. Tube 52 helps to reach overpouched PD fluid sets 12 and to accurately guide the WFI. Water injector or pump 50 receives WFI from WFI source 54 via hose 56 and is attached to mount 62, which moves the injector or pump back and forth. Mount 62 is machined (if metal, e.g., aluminum or stainless steel) or formed (if plastic, e.g., PVC, nylon, teflon) to have threads 64 (FIGS. 5A and 5B) that accept a ball screw or lead screw 66. Ball screw or lead screw 66 is turned to move mount 62 and thus water injector or pump 50 towards and away from side or edge 42 of conveyor 40 and overpouched PD fluid sets 12.

Lead screw or ball screw 66 is coupled to a motor 70 via a coupler 72. Coupler 72 in an embodiment is a slit flexible coupler that helps to prevent backlash between motor 70 and ball screw or lead screw 66, improving the positional accuracy of injector or pump 50 and its injector tube 52. Motor 70 can rotate in two directions and is accurately positionable. Motor 70 may be a stepper or servo motor. In the illustrated embodiment, motor 70 is mounted to a slide plate 68 of motorized gantry or linear actuator 60. Mount 62 slides along slide plate 68, which prevents the mount from turning with ball screw or lead screw 66.

In the illustrated embodiment of FIG. 4, system 10 includes three sensors 80, 90 and 100, each receiving power from and outputting to control unit 30. Sensor 80 is a trigger sensor. FIGS. 3 and 4 illustrate that trigger sensor 80 is in one embodiment located above and positioned to look down on conveyor 40. Trigger sensor 80 is adjustably fixed to a frame of system 10 via an adjustable mount 82. Adjustable mount 82 allows trigger sensor 80 to be adjusted width-wise across conveyor 40 to a desired set position. Trigger sensor 82 in one embodiment includes an emitter and a receiver. A laser, infrared or other type of optical beam is emitted from the emitter, reflects off of the belt of conveyor 40 and is retrieved at the receiver of sensor 80. Trigger sensor 80 senses when the leading edge LE (FIG. 4) of a moving overpouched PD fluid set breaks the beam, and outputs to control unit 30 accordingly. The receipt of the output at control unit 30 triggers control unit 30 of system 10 to perform the water injection sequence.

Sensor 90 is an overpouch location sensor. FIG. 4 illustrates that overpouch location sensor 90 is in one embodiment located along side or edge 42 of conveyor 40 and is positioned to look horizontally inward to find an open end 22*a* of an overpouched PD fluid set 12. Overpouch location sensor 90 in the illustrated embodiment is fixed to side or edge 42 of conveyor 40 via a mount 92. Overpouch location sensor 90 is in one embodiment a laser distance sensor that detects the distance D (FIG. 4) between the sensor and the front of open end 22*a* of overpouch 22 of overpouched PD fluid set 12. An output indicative of sensed distance D is sent from sensor 90 to control unit 30. Control unit 30 uses sensed distance D, or a calculated distance based upon sensed distance D (for example a calculated distance between side wall or edge 42 and overpouched PD fluid set 12 based upon sensed distance D), to determine how far to move water injector or pump 50 and its outlet tube 52 towards open end 22*a* of overpouched PD fluid set 12.

Suitable sensors 80 and 90 are provided for example by Keyence Corporation, Itaska, Illinois.

Sensor 100 is a water detection sensor. FIG. 4 illustrates that water detection sensor 100 is in one embodiment located directly adjacent and pointing towards the outlet tip of outlet tube 52 extending from water injector or pump 50. Water detection sensor 100 in the illustrated embodiment is fixed adjustably to a mount 102, which is in turn fixed to water injector mount 62. Water detection sensor 100 may be adjusted to the left or right in FIG. 4 to be further away from or closer to the tip of outlet tube 52 and then be set at a desired location. Water detection sensor 100 moves with water injector or pump 50 as mount 62 is translated via the turning of ball screw or lead screw. Water detection sensor 100 is in various embodiments a proximity sensor that creates a field, such as a magnetic field, that when disrupted causes a state change that is detected at control unit 30. There are different types or proximity sensors, such as inductive and capacitive sensors. Such sensors may be provided by the manufacturer listed above and many others.

The disruption that water detection sensor 100 is looking for is the WFI injection exiting from outlet tube 52. The water exiting outlet tube 52 disrupts the magnetic field of water detection sensor 100, causing the sensor to send a signal to control unit 30 indicating that overpouched PD fluid set 12 has actually received the WFI injection. In this manner, water detection sensor 100 allows system 10 to ensure that each overpouched PD fluid set 12 has actually received an injection of WFI.

In one embodiment, control unit 30 starts first and second internal timers when trigger sensor 80 senses the leading edge LE (FIG. 4) of overpouched PD fluid set 12. The time duration associated with the first timer is the time, based upon the speed of conveyor 40, that it takes for the middle of overpouched PD fluid set 12 to move directly in front of the center axis of outlet tube 52. At the conclusion of the time duration of the first timer, control unit 30 causes water injector or pump 50 to pump the preset amount or volume of WFI through outlet tube 52 and into the middle of overpouched PD fluid set 12. The time duration associated with the second internal timer is the WFI injection duration of the first timer plus an additional amount of time, such as a second or less. Control unit 30 is programmed such that if it does not receive an actual WFI injection confirmation from water detection sensor 100 within the second time duration, an assumption is made that a problem has occurred with water injector or pump 50 or WFI source 54. Control unit 30 accordingly alarms audibly and/or visually at display device 38 and shuts down conveyor 40 in one embodiment.

It is contemplated to provide a third timer having a third duration that is triggered by trigger sensor 80 sensing the leading edge LE (FIG. 4) of overpouched PD fluid set 12. The third duration is a duration in which control unit 30 expects (including a small additional amount of time for an engineering factor) to receive a distance indication signal from overpouch location sensor 90. Control unit 30 is programmed such that if it does not receive a distance indication signal from overpouch location sensor 90 within the third time duration, an assumption is made that a problem has occurred with overpouch location sensor 90. Control unit 30 accordingly alarms audibly and/or visually at display device 38 and shuts down conveyor 40 in one embodiment. As alluded to above, each of the first, second and third times is dependent upon the speed of conveyor 40. Control unit 30 is accordingly programmed in one embodiment such that the first, second and third time durations are determined by equations that are a function of the speed of conveyor 40. It is also assumed that the geometry of overpouched PD fluid sets 12 is constant. If the geometry changes, then the time durations may also need to change. In an embodiment, control unit 30 is programmed to store different time durations or different time duration equations for differently sized overpouched PD fluid sets 12.

FIG. 4 also illustrates that block 110 is located downstream from water injector or pump 50. After receiving WFI from water injector or pump 50, control unit 30 causes the overpouched PD fluid sets 12 to be conveyed along conveyor 40 through block 110. Block 110, as illustrated in more detail in connection with FIG. 6, forces an amount of air out of overpouch 22. Overpouch welder 116 in FIG. 4 welds open end 22*a* of overpouch 22 closed immediately after leaving air removing block 110. The humidity of the air within overpouched PD fluid sets 12 is increased accordingly due to the addition of WFI and the removal of air in one embodiment. In alternative embodiments, system 10 employs only one of the two humidity increasing procedures.

Figure 5A:
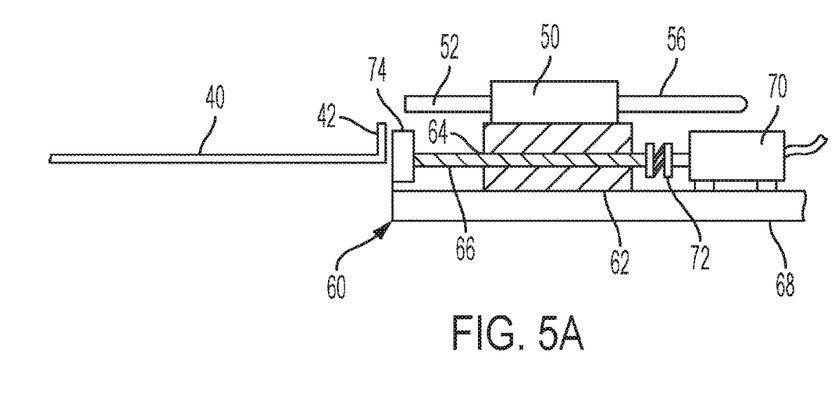
FIG. 5A is a side elevation view of one embodiment of a motorized gantry or linear actuator of the medical fluid container preparation system and associated methodology of the present disclosure in a first, non-pumping position.
Figure 5B:
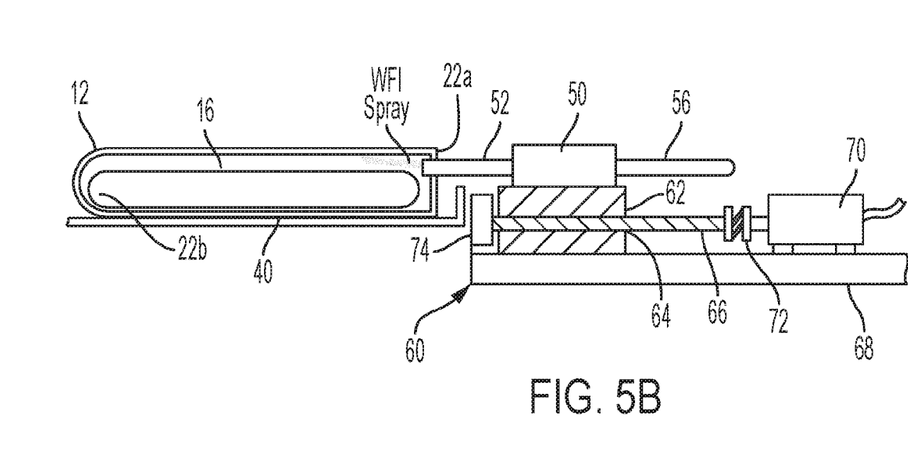
FIG. 5B is a side elevation view of the motorized gantry or linear actuator of FIG. 5A in a second, non-pumping position.

FIGS. 5A and 5B illustrate the structure and operation of water injector or pump 50 and motorized gantry or linear actuator 60 in more detail. Motorized gantry or linear actuator 60 includes slide plate 68, which is fixed directly or indirectly to the frame of system 10. Motor 70 is fixed to slide plate 68. A bearing flange 74 is also connected to slide plate 68 and is aligned with the shaft of motor 70. Bearing flange 74 holds a distal end of ball or lead screw 66. The proximal end of ball or lead screw 66 is connected to motor 70 via flexible coupler 72. Ball or lead screw 66 is threaded through threaded hole 64 in mount 62. Mount 62 slides along slide plate 68, which constrains mount 62 to translate along slide plate 68 when motor 70 under control of control unit 30 causes ball or lead screw 66 to turn. Turning ball or lead screw 66 in a first direction causes mount 62 to move towards conveyor 40, while turning ball or lead screw 66 in a second direction causes mount 62 to move away from conveyor 40. The accuracy of motor 70 allows water injector or pump 50 and its output tube 52 to be positioned precisely. In an embodiment, the acceleration and velocity of motor 70 may also be controlled and programmed into control unit 30.

FIGS. 5A and 5B also illustrate that hose 56, which is connected to source of WFI 54, is also connected to water injector or pump 50. Water injector or pump 50, under control of control unit 30, pulls WFI from source 54 via hose 56 as needed. Water detection sensor 100 under its operation described above detects when WFI source 54 is empty and needs to be refilled. FIGS. 5A and 5B further illustrate motorized gantry or linear actuator 60 positioned adjacent to conveyor 40 having side or edge 42, wherein conveyor 40 moves such that overpouched PD fluid sets 12 travel out of the page.

In FIG. 5A, no overpouched PD fluid set 12 is present and trigger sensor 80 (not illustrated) is not triggered. Control unit 30 accordingly causes mount 62 and water injector or pump 50 to be in a retracted position, where outlet tube 52 is not in the path of an incoming overpouched PD fluid set 12. In FIG. 5B, an overpouched PD fluid set 12 is present and trigger sensor 80 (not illustrated) is triggered. Overpouch 22 in FIG. 5B is shown in section, such that solution bag 16 is visible. After trigger sensor 80 is triggered, overpouch location sensor 90 (not illustrated) detects the location of open end 22a of overpouch 22 as discussed above.

Overpouch location sensor 90 sends a signal to control unit 30 indicative of the distance to open end 22a of overpouch 22, which control unit 30 uses to determine how far to cause motor 70 to move mount 62 and water injector or pump 50 along slide plate 68 (e.g., how many pulses for motor 70 to turn ball or lead screw 66). FIG. 5B illustrates that water injector or pump 50 is translated such that the distal end of outlet tube 52 resides just inside open end 22a of overpouch 22, and such that WFI spray is guaranteed to be fully delivered within overpouch 22, e.g., between the overpouch and solution bag 16. Water detection sensor 100 (not illustrated) senses the WFI spray as discussed above, and indicates the detection to control unit 30.

Figure 6:
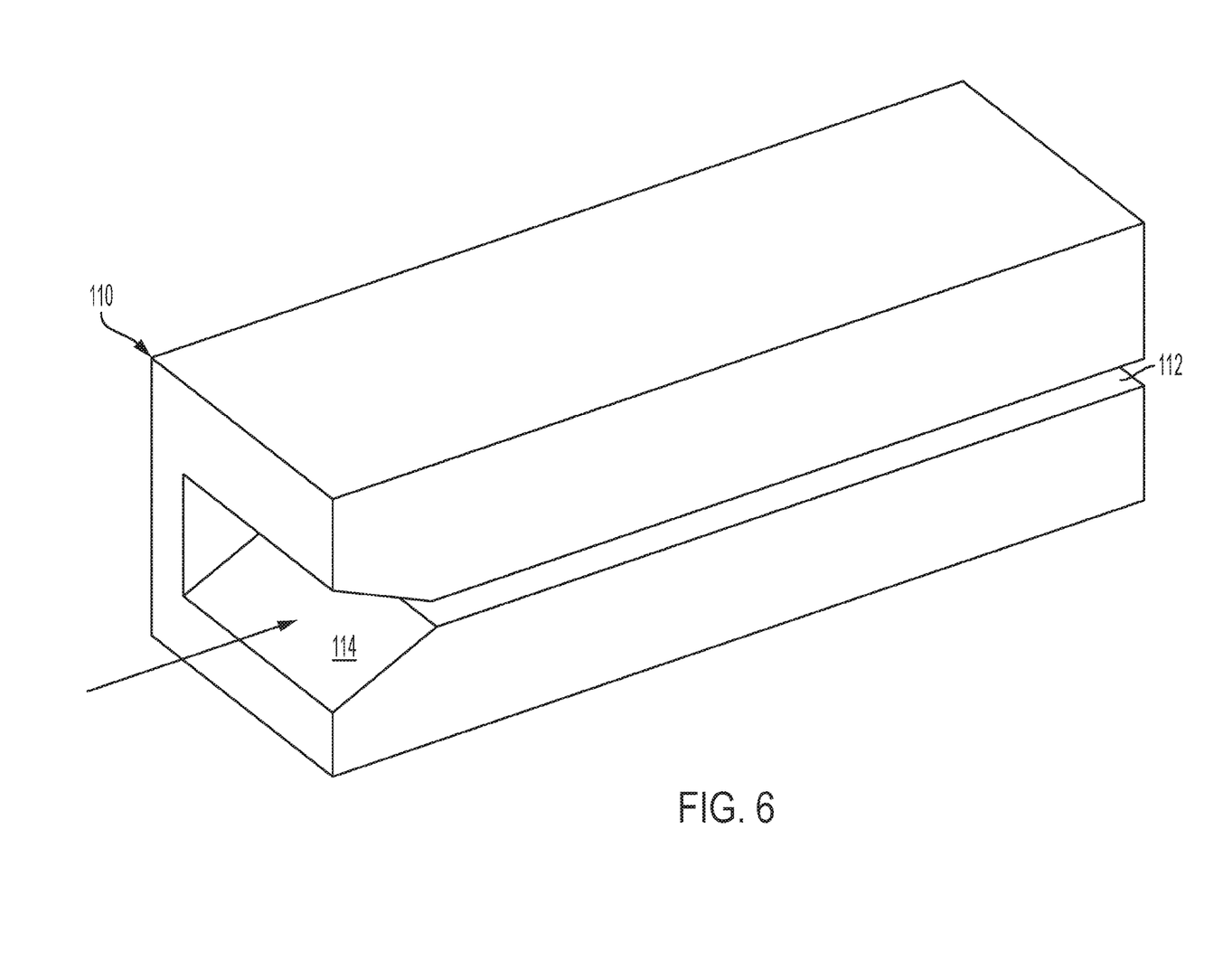
FIG. 6 is a perspective view of one embodiment of an overpouch squeezing block of the medical fluid container preparation system and associated methodology of the present disclosure.

As discussed above, the addition of WFI into overpouched PD fluid set 12 is one procedure contemplated to raise the humidity within the set. The other is to alternatively or additionally remove air from overpouched PD fluid set 12. FIG. 6 illustrates one embodiment of a block 110, which is located downstream of the WFI injection just described, and is mounted along side or edge 42 of conveyor 40 as illustrated in FIGS. 2 and 4. Block 110 is machined (if metal, e.g., aluminum or stainless steel) or formed (if plastic, e.g., PVC, nylon, teflon) to have a narrow groove 112 that squeezes together the sheets forming open end 22a of overpouch 22 of overpouched PD fluid set 12, which moves through groove 112 from left to right as illustrated by the arrow in FIG. 6. Tapered entry end 114 of groove 112 helps to transition open end 22a of overpouch 22 from its normal open shape (see FIG. 3) to the squeezed-down shape due to narrow groove 112. It is estimated that groove 112 removes from tens to hundreds of milliliters of air from overpouched PD fluid set 12 prior to open end 22a being welded closed via overpouch welder 116 located just downstream from block 110 in one embodiment.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims. For example, while the present systems and methods are described mainly in connection with peritoneal dialysis bags, it should be appreciated that the present system and methods are applicable to other types of parenteral fluid bags, such as blood treatment fluid bags, medical fluid delivery bags, saline bags and the like. Additionally, while the present systems and methods are described mainly in connection with medical fluid bags, it should be appreciated that the present system and methods are applicable to other types of medical fluid containers, such as more rigid medical fluid containers. Further additionally, while motorized gantry or linear actuator 60 is generally illustrated as being an electromechanical system employing a stepper or servo motor 70, it is contemplated to provide a different type of linear actuator, such as a pneumatically driven piston.

ELEMENT NUMBER LISTING

10—overpouch preparation system
12—overpouched PD fluid set
14—PD fluid set
16—PD solution bag
18—drain bag
20—Y-site
22—overpouch
22a—initially open end of overpouch
22b—closed end of overpouch
30—control unit
32—one or more processor of control unit
34—one or more memory of control unit
36—electronics of control unit
38—user interface/display device of control unit
40—conveyor
42—side or edge of conveyor
50—water injector or pump
52—tube connected to outlet of water injector or pump
54—source of water for injection ("WFI")
56—hose for connecting source of WFI to water injector or pum
60—motorized gantry or linear actuator
62—mount for water injector or pump
64—threaded hole in mount
66—ball screw or lead screw threaded through threaded hole in mount
68—slide plate
70—motor for driving lead screw
72—coupler for connecting motor to lead screw
74—bearing mount for connecting to distal end of lead screw
80—trigger sensor
82—mount for trigger sensor
90—overpouch location sensor
92—mount for overpouch location sensor
100—water detection sensor
102—mount for water detection sensor
110—block
112—groove in block
114—tapered entry end of groove
116—overpouch welder The invention is claimed as follows:

1. A medical fluid container preparation system comprising:
   a conveyor for conveying the medical fluid container;
   a water injector located along the conveyor;
   a mechanism for carrying the water injector towards and away from the medical fluid container;
   a sensor positioned and arranged to determine a location of the medical fluid container moving along the conveyor; and
   a control unit configured to read an output from the sensor and to cause (i) the mechanism to move the water injector towards the medical fluid container an amount based upon the location of the medical fluid container obtained from the sensor output and (ii) the water injector to inject a volume of water between the medical fluid container and an overpouch into which the medical fluid container is placed.

2. The medical fluid container preparation system of claim 1, wherein the location sensed by the sensor is a distance between the medical fluid container and a reference position of the conveyor.

3. The medical fluid container preparation system of claim 2, wherein the reference position includes the sensor or a side of the conveyor.

4. The medical fluid container preparation system of claim 1, wherein the sensor is a first sensor, and which includes a second sensor positioned and arranged to provide an output to the control unit for triggering movement of the water injector by the mechanism.

5. The medical fluid container preparation system of claim 4, wherein the second sensor is positioned and arranged above the conveyor and the medical fluid container.

6. The medical fluid container preparation system of claim 4, wherein the second sensor is focused on a location of the conveyor that is upstream of where the water injector traverses the conveyor.

7. The medical fluid container preparation system of claim 1, wherein the sensor is a first sensor, and which includes a second sensor positioned and arranged to provide an output to the control unit to ensure that the volume of water is injected between the medical fluid container and the overpouch.

8. The medical fluid container preparation system of claim 7, wherein the second sensor is secured so as to travel with the water injector.

9. The medical fluid container preparation system of claim 1, which includes a block located along the conveyor, the block including a groove that forces an open end of the overpouch to partially close, the partial closure forcing a desired quantity of air out of the overpouch.

10. The medical fluid container preparation system of claim 9, which includes an overpouch welder positioned and arranged downstream of the block to weld closed the open end of the overpouch before the removed quantity of air can reenter the overpouch.

11. The medical fluid container preparation system of claim 1, which includes a source of water in fluid communication with the water injector.

12. The medical fluid container preparation system of claim 1, wherein the water injector includes a positive displacement piston pump for injecting the volume of water between the medical fluid container and the overpouch.

13. The medical fluid container preparation system of claim 1, wherein the mechanism includes a motorized gantry or linear actuator.

14. The medical fluid container preparation system of claim 1, wherein the mechanism incudes a mount, a lead screw and a motor, the water injector mounted to the mount, the mount threadingly coupled to the lead screw, the lead screw driven by the motor.

* * * * *